United States Patent [19]

Komatsu et al.

[11] Patent Number: 4,937,764
[45] Date of Patent: Jun. 26, 1990

[54] METHOD OF OPTICAL DENSITY MEASUREMENT AND APPARATUS THEREFOR

[75] Inventors: Tomoaki Komatsu; Sigeo Satou, both of Tokyo, Japan

[73] Assignee: Fuji Photo Film Co., Ltd., Kanagawa, Japan

[21] Appl. No.: 191,121

[22] Filed: May 6, 1988

[30] Foreign Application Priority Data

May 6, 1987 [JP] Japan .............................. 62-67654[U]
May 6, 1987 [JP] Japan .............................. 62-67655[U]
May 6, 1987 [JP] Japan .................................. 62-110296

[51] Int. Cl.$^5$ ................................................ G01N 21/17
[52] U.S. Cl. ................................. 364/558; 356/425; 356/432; 364/525; 364/571.01
[58] Field of Search ............... 364/525, 550, 558, 707, 364/571.01, 571.02; 356/73, 136, 432, 445, 425, 416, 448, 435, 319

[56] References Cited

U.S. PATENT DOCUMENTS

| | | | |
|---|---|---|---|
| 3,970,393 | 7/1976 | Krygeris et al. | 356/425 |
| 4,082,458 | 4/1979 | Fukui et al. | 356/432 |
| 4,242,730 | 12/1980 | Golias et al. | 356/432 |
| 4,473,298 | 9/1984 | Sakamoto | 356/432 |
| 4,645,350 | 2/1987 | Weidmann et al. | 356/446 |
| 4,667,289 | 5/1987 | Yoshida et al. | 364/707 |
| 4,696,570 | 9/1987 | Joliot et al. | 356/319 |
| 4,750,837 | 6/1988 | Gifford et al. | 356/319 |
| 4,762,412 | 8/1988 | Ohkubo et al. | 356/319 |

Primary Examiner—Kevin J. Teska
Attorney, Agent, or Firm—Young & Thompson

[57] ABSTRACT

A method of measuring optical density is characterized by the steps of measuring reflected light from a subject being measured a plurality of times during a predetermined interval, and calculating a mean value of the plurality of measured values. For providing the zero point correction data, the known standard optical densities are previously set in the densitometer. A densitometer for practicing the calibrating method is formed compact and handy and comprises a housing in which measuring elements such as a light projecting member, a light receiving member and a reference light detecting member are incorporated. In the housing are further provided circuits for calculating a density based on outputs from the light receiving and reference light detecting members and for battery power checking. The housing includes a transparent panel formed with a measuring aperture by which a measuring area of a subject is defined.

22 Claims, 11 Drawing Sheets

OPTICAL DENSITY MEASUREMENT SEQUENCE

METHOD OF OPTICAL DENSITY MEASUREMENT AND APPARATUS THEREFOR

BACKGROUND OF THE INVENTION

The present invention relates to a method of calibrating a measured optical density and apparatus for practicing this method by the use of standard optical density plates.

Two types of optical densitometers are well known: transmitted-light densitometers for detecting transmission densities of measured subjects, and reflected-light densitometers for detecting reflection densities of measured subjects. These densitometers are widely used in image recording such as photography, printing and so on to measure characteristics of image recording materials or images recorded on image recording materials. In scientific measurement fields, a film for measuring pressure is used together with a reflected-light densitometer. This pressure-measuring film changes color or magenta density with pressure change. The film is placed where the pressure is applied so to be changed in color. Then, the colored film is measured to detect reflection density. With reference to a conversion table of density to pressure, the pressure is obtained from the measured optical density.

Conventional optical densitometers comprise a body incorporating various elements such as operation circuits, meters, a power source and the like; and a separate measuring head connected to the body for detecting reflected or transmitted light from a subject to be measured. Such a separate measuring head is provided with a light projecting means for projecting light toward the subject, a light receiving means for receiving light from the subject, and a reference light detecting means for detecting a part of the projected light as a reference light.

Generally, when using a densitometer, it is necessary to perform a zero point correction of the densitometer prior to an actual measurement of a subject for the purpose of avoiding errors caused by extraneous factors such as temperature and conditions of ambient light, and by internal factors such as changes of lamp and light receiving elements due to aging. For the zero point correction, members having known densities are measured to compensate for a difference between a measured density and an actual density.

In practice, a low standard density member is measured by the densitometer to be corrected. According to the measured value, which is referred to as a standard value of low density, the needle of a meter of the densitometer is adjusted to register the standard value of low density. Thereafter, a high standard density member is measured by the densitometer. In the same manner, the meter needle is adjusted to register the standard value of high density. The adjustment is repeated several times so as to adjust the meter needle to register the standard values of known low and high densities for zero point correction.

In the conventional zero point correction methods, several needle adjustments are needed to make a zero point correction which is quite a troublesome operation.

The conventional densitometers, because of their separate body and measuring head, are inconvenient to handle and transport. Such a measuring head has a measuring surface attached to a light shielding plate formed with a measuring aperture which is positioned on a subject to be measured. Therefore, if the subject is small, it is troublesome to accurately position the measuring aperture of the subject.

OBJECTS OF THE INVENTION

It is, therefore, an object of the present invention to provide a method and apparatus for calibrating measured values of optical density requiring no adjusting operation for zero point correction.

It is another object of the present invention to provide a compact optical densitometer which is convenient to use and is handy to carry.

SUMMARY OF THE INVENTION

The method of calibrating a measured value of optical density according to the present invention comprises the steps of measuring members of known high and low standard density to detect their density values, obtaining and memorizing or storing zero point correction data based on the differences between the measured values of standard densities and the known standard density values, and calibrating the measured value of density of a subject by using the zero point correction data. This zero point correction data is an expression comprising a coefficient term and a constant term. When $\alpha$, $K$ and $R_D$ are a coefficient, a constant and a measured value of density, respectively, a calibrated measured value $R$ of density is given by the following equation:

$$R = R_D - \alpha . R_D - K.$$

An apparatus for practicing the method of calibrating a measured value of density according to the present invention comprises an upright body housing incorporating operation circuits, a display panel, a power source circuit and the like, with their associated elements, and a measuring head attached to a bottom of the housing. This measuring head is formed with an opening defined by a recess extending between a bottom side and a front side thereof. The opening in the bottom of the measuring head is covered by a transparent plate with an inverse frustoconical measuring aperture under which a subject to be measured is placed. The subject is measured to detect a reflection density through the aperture which has an inner surface painted black.

There is also provided a case to receive the densitometer for protection and carrying. When using the densitometer, the case is used to conveniently introduce a zero point correction. For this purpose, the case is provided with standard high and low known density plates or blocks on the inner bottom plate thereof. By putting the densitometer on the inside bottom of the case, a zero point correction is effected with ease.

The densitometer according to the present invention avoids the operation of an adjusting member which is conventionally used to effect a zero point adjustment. The densitometer, which is made as one body, is convenient to use and handy to carry. According to the present invention, the densitometer has a measuring aperture formed in a transparent plate attached to the bottom of a measuring head including light projecting and light measuring means. This makes it quite easy to position the measuring aperture on a subject whose optical density is to be measured. The measuring aperture, which is shaped in the form of an inverse frustum and has an inner surface painted black, diminishes undesirable reflected light impinging thereto.

In addition, the measuring method of the present invention is characterized by the use of a mean value of a plurality of measured values, so that an accurate optical density measurement is effected. The densitometer of this invention is adapted to interrupt a measurement and provide a warning when battery power is lower than a predetermined level, so as to eliminate erroneous measurements. By providing a carrying case incorporating standard density plates used to make a zero point correction, misplacing standard density plates as with conventional densitometers is avoided.

BRIEF DESCRIPTION OF THE DRAWINGS

The above and other objects and features of the invention will be apparent from the following description taken along with the preferred embodiment thereof with reference to the accompanying drawings, wherein.

DETAILED DESCRIPTION OF THE INVENTION

Figure 1:
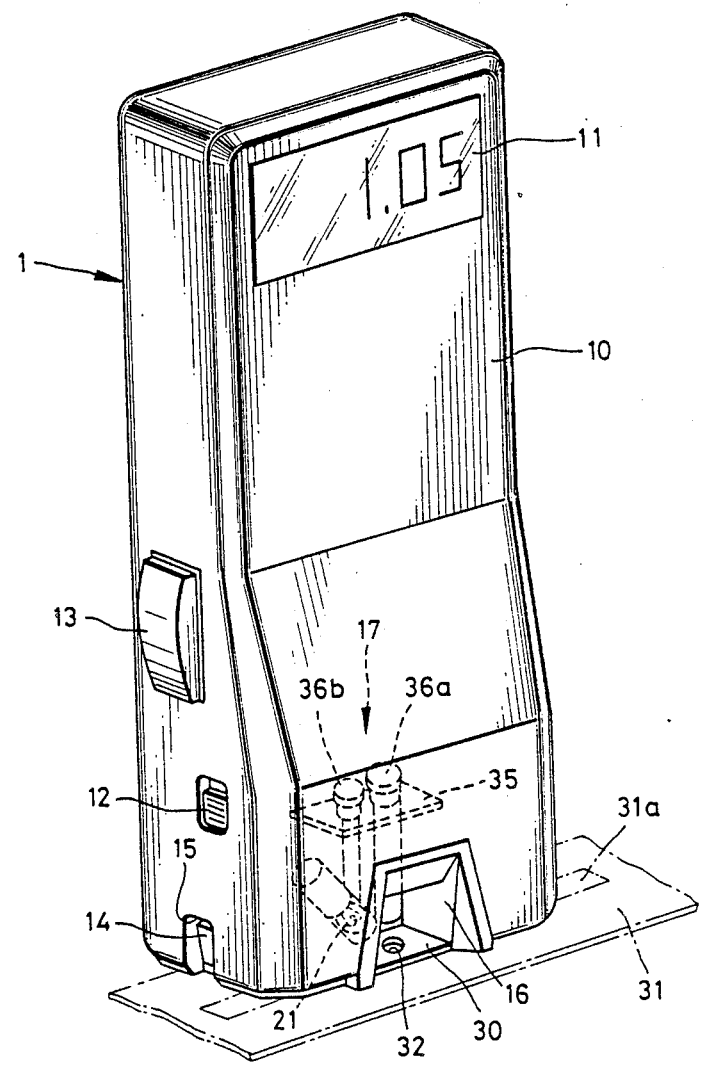
FIG. 1 is a perspective view showing the outer appearance of a densitometer which embodies the present invention.

Referring now to FIG. 1, there is shown a reflected-light optical densitometer embodying the present invention. As shown, the densitometer, which incorporates a measuring head therein, is handy and portable. The densitometer 1, which is preferably made of plastic materials, has a generally rectangular box-shaped upright housing 10 which is broader toward the bottom for stability during use. The housing 10 of the densitometer 1 is provided with a digital display panel 11 attached to an upper section of a front wall thereof for displaying a measured value of density thereon, a slidable power switch 12, a pushbutton switch 13 for starting measurement and a switch 14 for effecting a zero point correction, all of the switches 12, 13 and 14 being provided in a side wall of the housing. The switch 14 is disposed within a recess 15 and below the surface of the side wall to prevent accidental operation.

Figure 2:
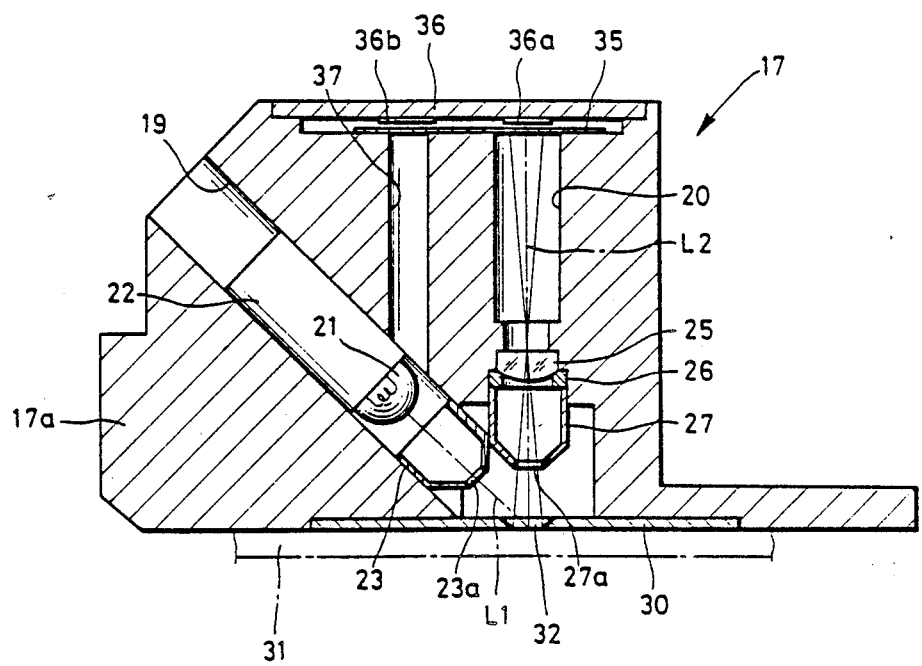
FIG. 2 is a cross sectional view of a measuring head incorporated in the densitometer of FIG. 1.
Figure 3:
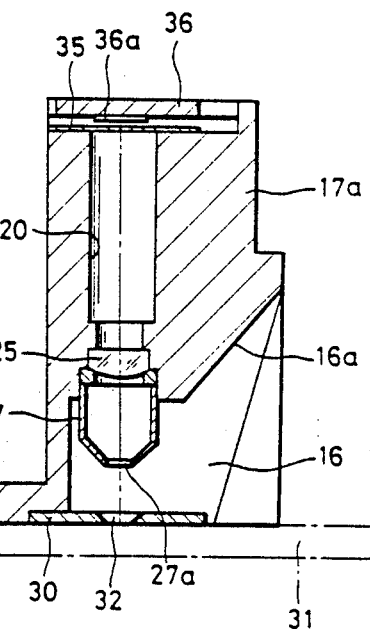
FIG. 3 is a side cross sectional view showing the measuring head of FIG. 2.

At the bottom of the housing 10, a measuring head assembly 17 is attached. As shown in FIGS. 2 and 3, the measuring head assembly 17 has a head block 17a made of heat-resisting plastic materials such as ABS resins. The choice of materials for the head block 17a is made in consideration of the prevention of radiation from a lamp from being transmitted, even if slightly, to a circuit board including a light receiving element and an amplifier. The head block 17a is formed with through-holes 19 and 20 reaching an opening 16. The opening 16 is formed in the front and bottom sides of the head block 17a and has an inclined upper wall surface 16a affording observation from above by an operator. The through-hole 19 is inclined at about 45° and receives therein a lamp holder 22 holding a lamp 21 therein for projecting light toward a subject 31 to be measured. In the lower end of the through-hole 19 there is a light tight barrel 23 with an opening 23a formed at its bottom end. This opening 23a acts as a fixed field stop to control the beam of light from the lamp 21.

The through-hole 20 is vertically arranged in the head block 17a relative to the bottom to fixedly receive a lens 25 retained therein by means of a retaining ring 26. At the bottom of the through-hole 20 there is mounted a light tight barrel 27 with an opening 27a formed at its bottom end which acts as a fixed field stop for the lens 25.

Figure 4:
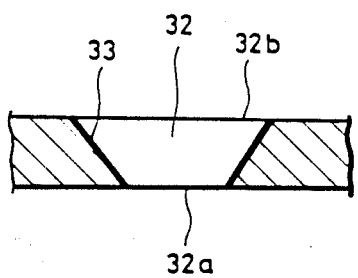
FIG. 4 is an enlarged cross sectional view showing part of a transparent plate attached to the bottom of the measuring head of FIG. 2.

The bottom of the opening 16 is provided with a transparent plate 30 flush with the under surface of the head block 17a. The transparent plate 30 allows the subject 31 to be viewed therethrough. This transparent plate 30 contains an inverse frustoconical measuring aperture 32 narrowing toward the bottom at an intersection of optical axes L1 and L2 of the light beam and the lens 25. As is shown in detail in FIG. 4, the measuring aperture 32 has a bottom edge 32a reduced in diameter, for example to about 2 mm, in order to make it possible to measure a narrow or small subject. In an attempt to uniformly illuminate the bottom edge 32a of the measuring aperture 32, the center section of the measuring aperture 32 has an inner wall tapered at about 45°. In this embodiment, the top edge 32b of the measuring aperture 32 has a diameter of about 4 mm. The inner wall of the measuring aperture 32 is painted black as shown at 33 in FIG. 4 to prevent light directed thereon from the lamp 21 from being reflected back toward the measuring system and to prevent a part of the light reflected by the subject 31 from passing therethrough.

At the top of the head block 17a is a filter 35 for transmitting a specified wavelength range of light reflected from the subject 31. In this embodiment, a green filter is used to transmit light having a wavelength range of magenta. Over the filter 35, the head block 17a is provided with a circuit board 36 including two light receiving elements 36a and 36b, a logarithmic amplifier, and so forth. The light receiving element 36a is located above the through-hole 20 to receive and photoelectrically convert the reflected light from the subject 31. The other light receiving element 36b, which is located over a vertical through-hole 37 communicating with the through-hole 19 is provided to pick up a part of light emitted from the lamp 21 as a reference light. It is to be noted that if a black-an-white density is desired to be detected, the filter 35 can be omitted and that interchangeable filters make it possible to detect three color reflection densities.

Figure 5:
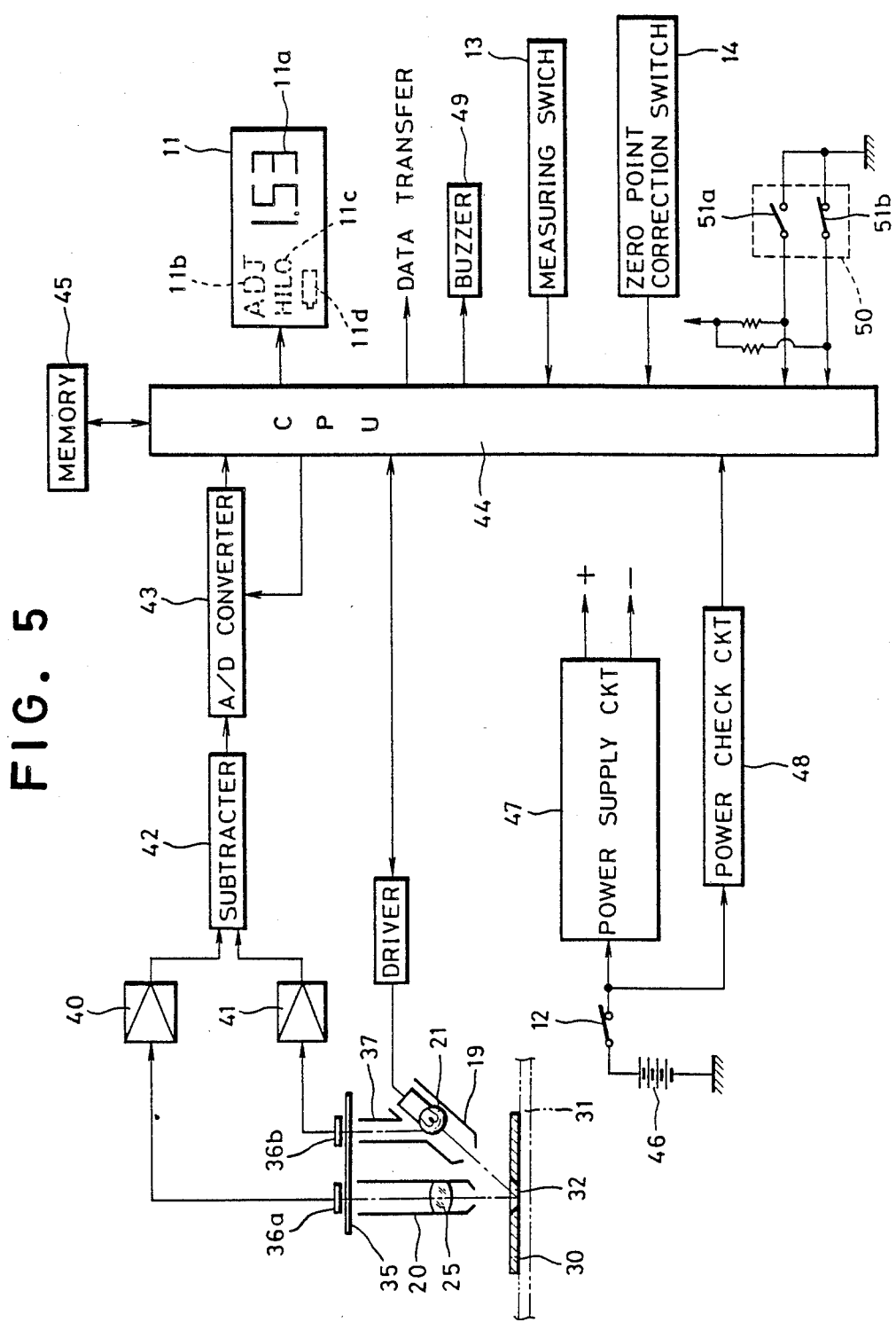
FIG. 5 is a block diagram showing a circuit embodying the method of the present invention.

Referring now to FIG. 5 showing a control circuit used in the optical densitometer 1, outputs from the light receiving elements 36a and 36b are sent to logarithmic amplifiers 40 and 41, respectively, and transformed into logarithms. Each logarithmic output from the amplifiers 40, 41 is processed by a subtracter 42 into a density signal which is periodically converted by an A/D converter 43 into a digital signal as a measured value of density. The number N of density values thus digitally converted are fed to CPU 44 and memorized in a memory 45. The CPU 44 is provided to sequentially control various elements in a programmed control of operation memorized or stored in the memory 45.

In the housing 10 of the densitometer 1, a plurality of batteries 46 are exchangeably loaded and connected to a power supply circuit 47 and a power check circuit 48 through the power switch 12. This power supply circuit 47 supplies a constant power of voltage to various electric elements when the power switch 12 is turned on. Four unit-3 batteries 46 loaded in the densitometer 1 allow approximately 10,000 measurements. When more than 10,000 measurements are carried out, the available power of these batteries 46 will gradually decrease. If the available power of the batteries 46 decreases below a certain level, the lamp 21 and logarithmic amplifiers 40 and 41 will change in their designed specific characteristics, resulting in erroneous measurements. To prevent such erroneous measurements, the battery check circuit 48 is provided to detect the present voltage of the batteries 46 and to send a warning signal indicating a change in battery voltage to the CPU 44 when it is lower than a certain level.

A liquid crystal display panel is preferably used for the display panel 11 to display four digit numbers 11a, an indication 11b of zero point calibration mode by a symbol "ADJ", a density level indication 11c "HI" or "LO" which means that a high or a low standard density is or was measured in the zero point correction mode, and a symbol mark 11d of a battery indicating a change in battery voltage. In the memory 45, there are stored a number of channels of combinations of various high and low standard density values. One of these channels is selected through a channel selection circuit 50 based on high and low standard densities obtained as a result of measurement of the high and low density plates. This selection of channels is ordinarily made by the manufacturer of the densitometer 1. For selecting one of, for example in this embodiment, four channels, there are two dip switches 51a and 51b. According to coded signals provided by these dip switches 51a and 51b, a desired channel is designated. Shown at 49 in FIG. 5 is a buzzer.

Figure 6:
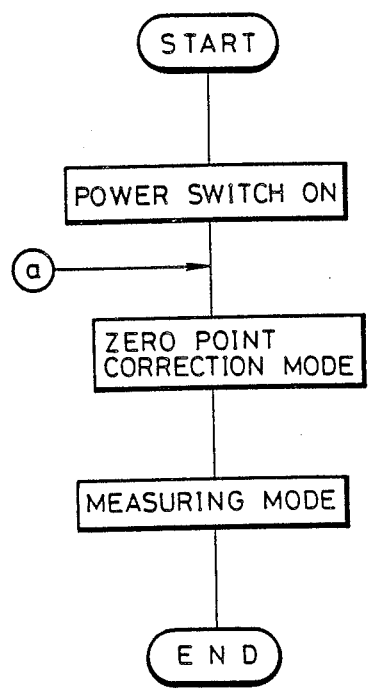
FIG. 6 is a flow chart showing a general sequence of measurement.

Referring now to FIGS. 6 to 10, a detailed explanation of measurement will be described. In FIG. 6 which is a flow chart of the general sequence of measurement, a first step in FIG. 1 is to turn on the power switch 12. Consequently, the densitometer 1 is shifted into the zero point correction mode of operation at a second step. Then, the densitometer 1 is shifted into the measurement mode of operation periodically to measure the subject 31 until the power switch 12 is turned off.

Figure 7:
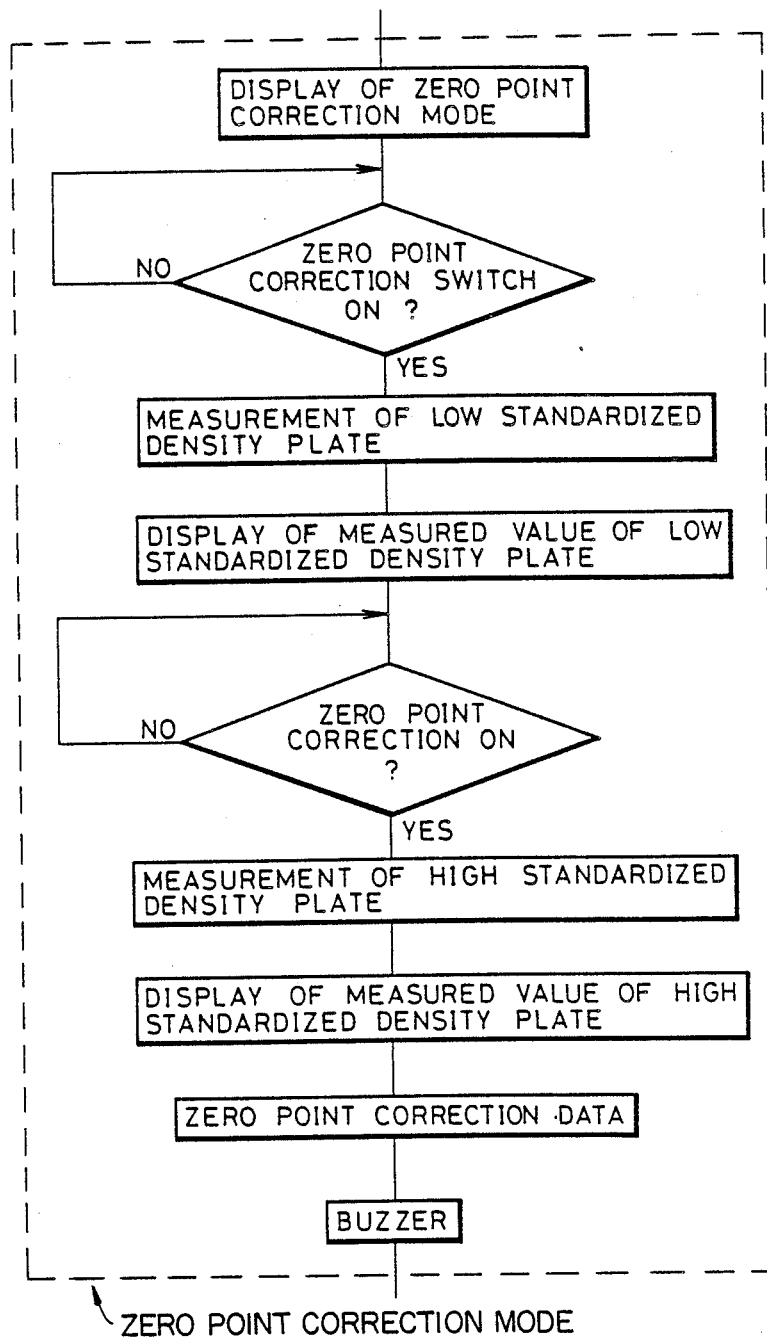
FIG. 7 is a flow chart of a zero point correction mode of operation.

In the zero point correction mode of operation, as is shown in FIG. 7, the densitometer 1 causes the display panel 11 to flash a four digit number 11a, the zero point correction mode indication "ADJ" 11b, and a density level indication 11c "HI" or "LO". After the transition of operation mode to the zero point correction mode, the densitometer 1 is put on a case (which will be described in detail later) to measure the high and low standard density plates attached to the case so as to provide zero point correction data. Specifically, when putting the densitometer 1 on a specified position of the case, the transparent plate 30 of the densitometer is brought into contact with the standard density plates H and L (which can be seen clearly in FIG. 12) and, simultaneously, the zero point correction switch 14 is turned on by means of a projection provided on a side wall of the case to start a measurement. Either one of the standard density plates may be measured first.

Figure 10:
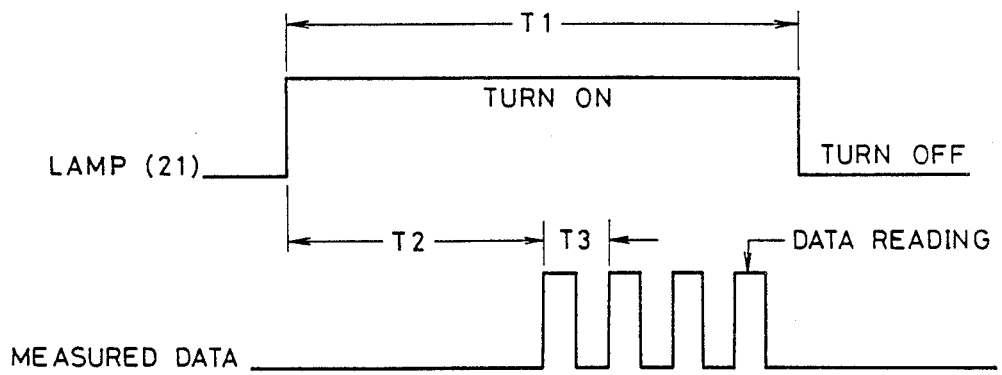
FIG. 10 is a timing chart showing a relationship between the data retrieval and lamp flashing.

As is shown in FIG. 10, as soon as the measurement is started, the lamp 21 is energized for a predetermined duration of time T1, for example 0.9 sec., to illuminate the standard density plate H or L with a spot light formed by the bottom opening 23a of the light tight barrel 23 through the aperture 32 of the transparent plate 30. The light reflected by the subject 31 passes through the measuring aperture 32 and the light tight barrel 20 and reaches the light receiving element 36a through the lens 25 and filter 35. The light receiving element 36a provides an output corresponding to an intensity of the received light. On the other hand, a part of the light emitted from the lamp 21 is received as a reference light by the light receiving element 36b. The light receiving element 36b provides an output corresponding to an intensity of the received light.

The outputs from the light receiving elements 36a and 36b are logarithmically transformed and amplified by the logarithmic amplifiers 40 and 41, respectively, and then sent to the subtracter 42 wherein a difference between the two outputs is obtained as a reflection optical density signal. Following this subtraction, the density signal is subjected to an analog-digital conversion in the A/D converter 43. As long as the power switch 12 is maintained turned on, the light receiving elements 36a and 36b, the logarithmic amplifiers 40 and 41 and others are kept under operation and the reflection density signal is periodically continuously provided by the subtracter 42 even though the lamp 21 is turned off. However, as will be described below, the reflection density signal is picked up only when the lamp 21 is maintained turned on.

Figure 8:
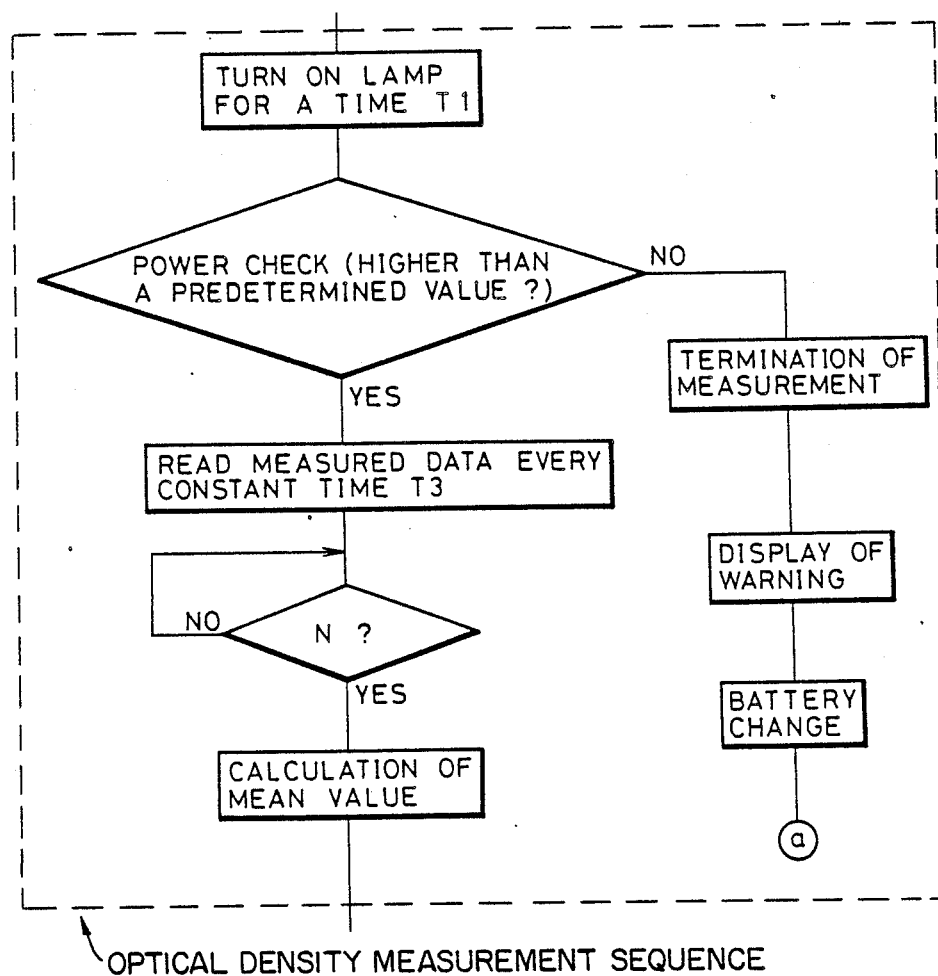
FIG. 8 is a flow chart showing a sequence of data retrieval.

As is shown in FIG. 8, after the lighting of the lamp 21, the CPU 44 retrieves an output from the power check circuit 48 to check the voltage of the batteries 46 above the predetermined level before picking up the measured reflection density data. The power check circuit 48 compares the present voltage of the batteries 46 with a reference voltage by means of a comparator to provide a binary signal for warning if the voltage of the batteries 46 is lower than the reference voltage. If the warning binary signal is presented, the CPU 44 stops the sequential control of operation and displays and flashes the battery mark 11d, the four digit number 11a, the zero point correction mode "ADJ" 11b, and the density level "HI" or "LO", with a certain periodic time. At this time the buzzer 49 is activated to give a positive warning indicating a change in battery voltage. With a change in battery voltage, the densitometer 1 is returned to the zero point correction mode of operation.

As is shown in FIG. 10, when a duration of time T2 (for example 0.5 sec.), which is the time required for the lamp 21 to reach a stable luminance intensity, has passed, the CPU 44 drives the A/D converter 43 with a predetermined periodic time T3 (for example 0.1 sec.) to effect a plurality of times, for example four times, of A/D conversions. The A/D converter 43 can sample reflection density signals provided by the subtracter 42 four times to convert these into digital signals (measured reflection density data). This sampling is substantially equivalent to that of the subject being measured four times. The resulting four density signals are sent to the CPU 44 and then stored in the memory 45. In the case where the voltage of the batteries 46 is lower, since the CPU 44 provides no indication, the A/D converter 43 doesn't operate and, therefore, no density signal is sent to the CPU 44.

Because data of the four density signals may possibly be scattered due to a change of luminance of the lamp 21 with time, transitional characteristics of the logarithmic amplifiers 40, 41, noises and the like, a mean value is obtained from two of the four density signals other than the maximum and minimum values. This mean value is referred to as a measured value of standard density.

Since certain high and low standard densities are designated through the channel selecting circuit 50, the actual measured values of the standard density are examined to determine to which standard density it resembles. For example, if the measured value of standard density is similar to a low standard density $R_1$, it is determined that the low standard density plate is measured and the level indication 11$b$ "LO" is displayed on the display panel 11. Simultaneously, the four digit number 11$a$ indicating the measured value of density and the indication "ADJ" 11$b$ are displayed on the display panel 11. For the purpose of indicating that the measurement is effected in the zero point correction mode, the display panel 11 flashes.

Thereafter, another standard density plate, for example a high standard density plate, is measured in the same way as described above with reference to FIG. 8. The resultant value is digitally displayed on the display panel 11 as well as the indications "HI" and "ADJ".

Figure 11:
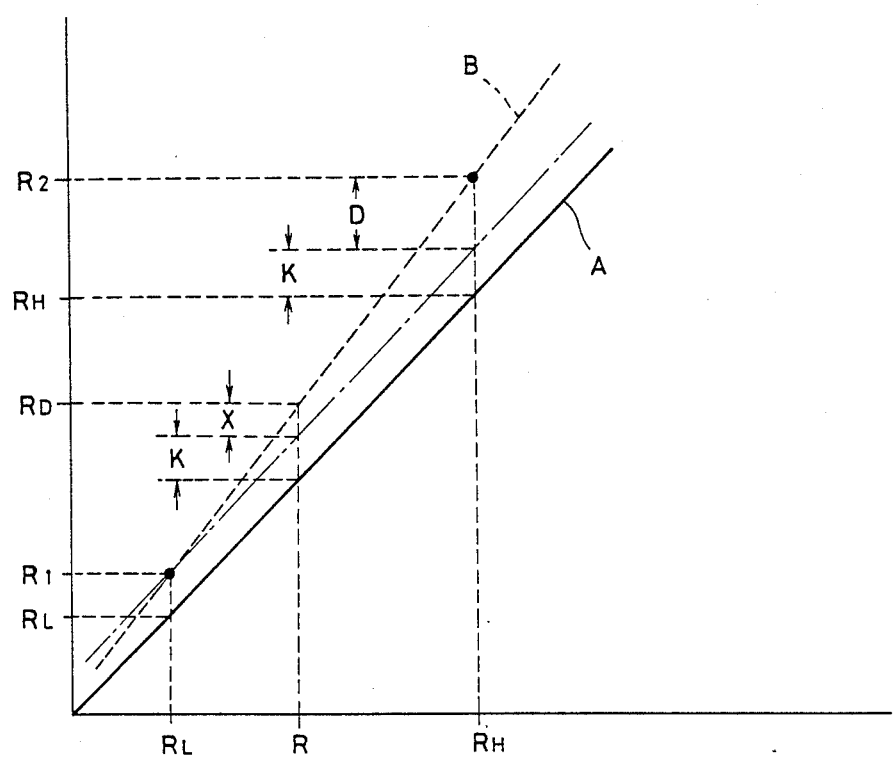
FIG. 11 is an explanatory graph for the zero point correction data.

After the completion of measurement of the high and low standard density plates, the CPU 44 provides zero point correction data. As is shown in FIG. 11, there are two density lines A and B, one shown by a solid line being representative of proper standard densities and the other shown by a dashed line being representative of actual measured densities, between which there are differences. In FIG. 11, $R_L$ and $R_H$ represent a low standard density value of the low standard density plate preset by a designation of a channel and a high standard density value of the high standard density plate preset by the designation of a channel, respectively. $R_1$ and $R_2$ are measured standard density values of the low and high standard density plates, respectively.

When drawing a straight line (shown by a chain line) passing the low density standard value $R_1$ and in parallel with the standard density line A, a measured value of density $R_D$ is calibrated as a value of density R by using the following expression:

$$R = R_D - X - K \quad (1)$$

where K is a constant term independent from the measured value of density $R_D$ and X is a coefficient term varying in accordance with the measured value of density $R_D$ and expressed by $X = \alpha \cdot R_D$ (wherein $\alpha$ is a coefficient).

Therefore, the calibrating expression (1) can be rewritten as follows:

$$R = R_D - \alpha \cdot R_D - K \quad (2)$$

The coefficient and the constant K are expressed as follows:

$$K = R_1 - R_L \quad (3)$$

$$= [(R_2 - R_H) - K]/(R_2 - R_1) \quad (4)$$

By substituting the coefficient $\alpha$ and the constant K in the calibrating expression (2), the following expression is obtained:

$$R = R_D \left[ 1 - \frac{(R_2 - R_H) - (R_1 - R_L)}{(R_2 - R_1)} \right] - (R_1 - R_L) \quad (5)$$

The CPU 44 calculates the constant K and the coefficient $\alpha$ by using the expressions (3) and (4), the result of the calculation being stored as zero point correction data in the memory 45. After the completion of providing the zero point correction data and the memorization thereof, the CPU 44 operates the buzzer 49 so as to indicate that a zero point correction mode has been finished. Simultaneously, the indications "ADJ" and "HI" disappear and the display panel 11 shifts into its continuous indication mode from flashing indication mode. In practice, since the zero correction data is provided before the indication of the display panel 11 becomes off-cycle, the lastly measured value of density is indicated substantially continuously.

For measuring a density of the subject 31, the densitometer 1 is put on the subject 31 to be measured as is shown in FIG. 1. By watching the subject 31 through the front opening 16, a measured area 31$a$ of the subject 31 is easily placed under the measuring aperture 32. Thereafter, the measuring switch 13 is pushed to start a measurement.

Figure 9:
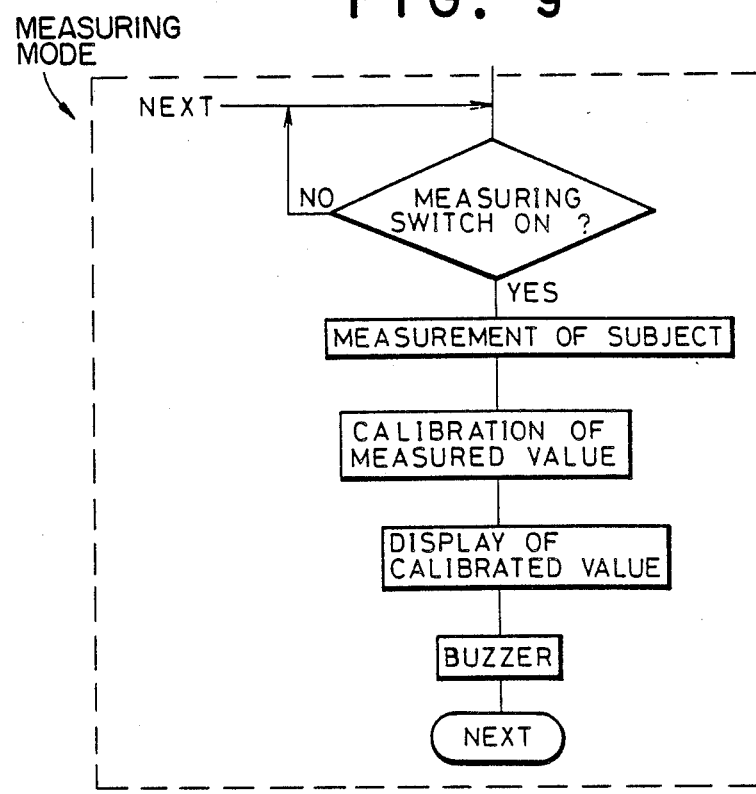
FIG. 9 is a flow chart showing a sequence of measurement.

As is shown in FIG. 9, when the measuring switch 13 is pushed and turned on, the lamp 21 is energized for a short time to emit light. During this short time light emission, the batteries 46 are checked and a plurality of data are obtained. Based on the obtained data, a measured value of density is calculated as to the subject 31. This measured value of density is calibrated by using the correction data obtained in the zero point correction mode. Specifically, the CPU 44 reads out the coefficient $\alpha$ and the constant K memorized in the memory 45 and substitutes these in the calibration expression (2) for calculating a calibrated measured value.

For example, when the values of $R_L$, $R_H$, $R_1$ and $R_2$ are 0.05, 1.30, 0.08 and 1.40, respectively, the coefficient $\alpha$ and the constant K are given as follows:

$$\alpha = 0.05$$

$$K = 0.03.$$

If the measured value is 1.00, the calibrated measured value R is obtained by substituting the coefficient and constant into the expression (2) as 0.98. This calibrated measured value is displayed on the display panel 11 and the buzzer 49 is operated to indicate that a measurement is finished. This indication of the calibrated measured value R is continuously held until the next measurement starts.

By connecting a printer to the densitometer 1, it is possible to make a data transfer to the printer to print out the data on reflection density values and their reduced values.

Figure 12:
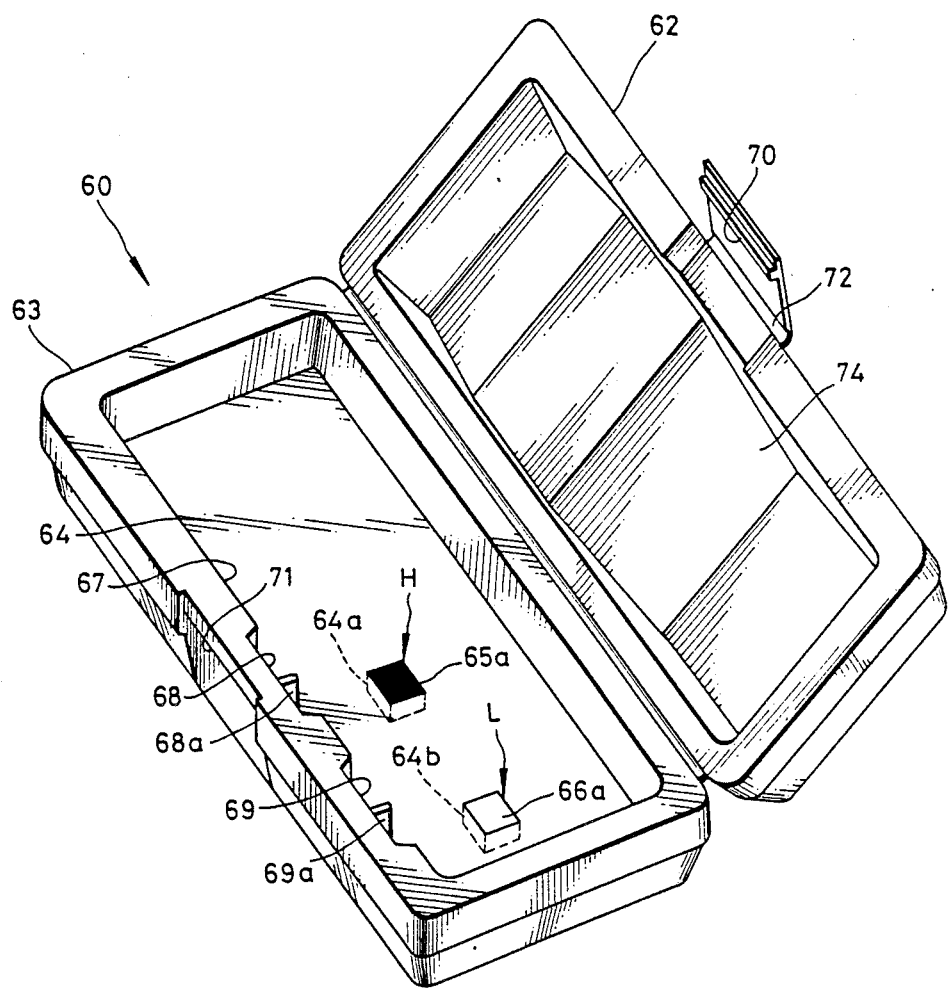
FIG. 12 is a perspective view showing a case with the cover opened.
Figure 13:
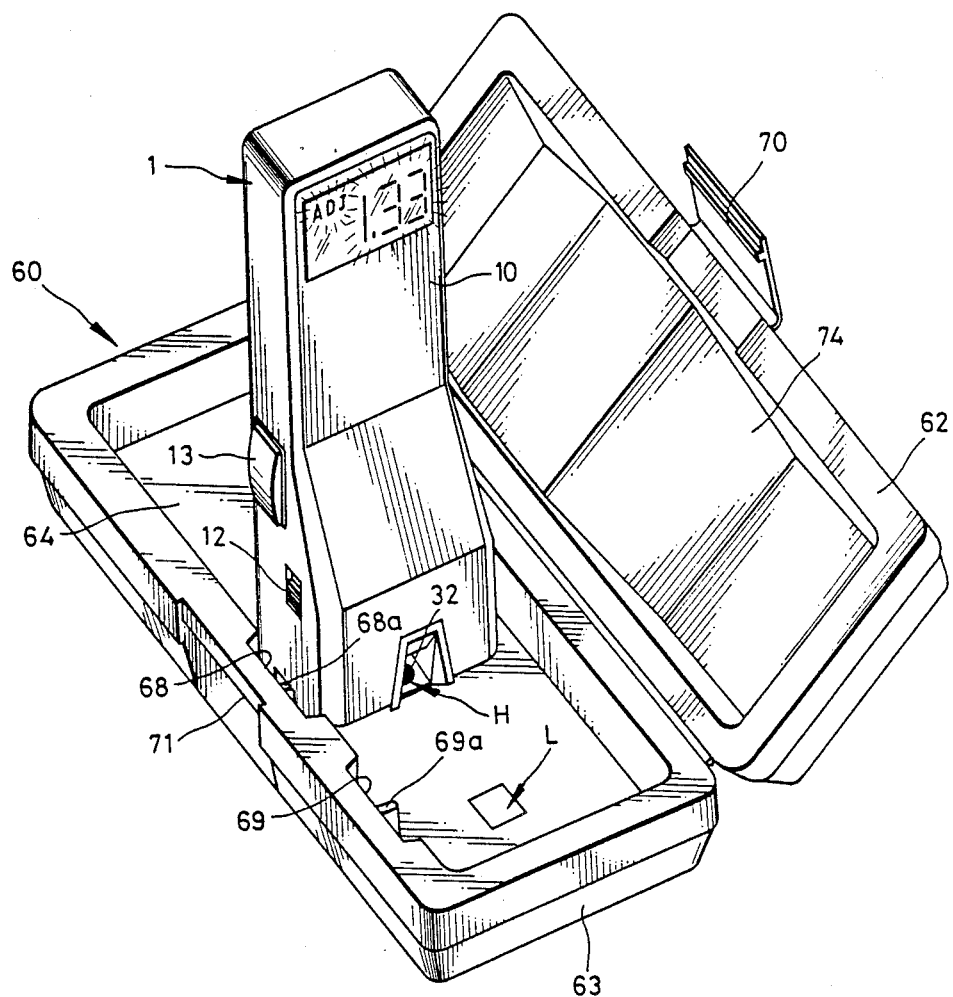
FIG. 13 is a perspective view showing the case of FIG. 12 which is used to effect a zero point correction measurement.
Figure 14:
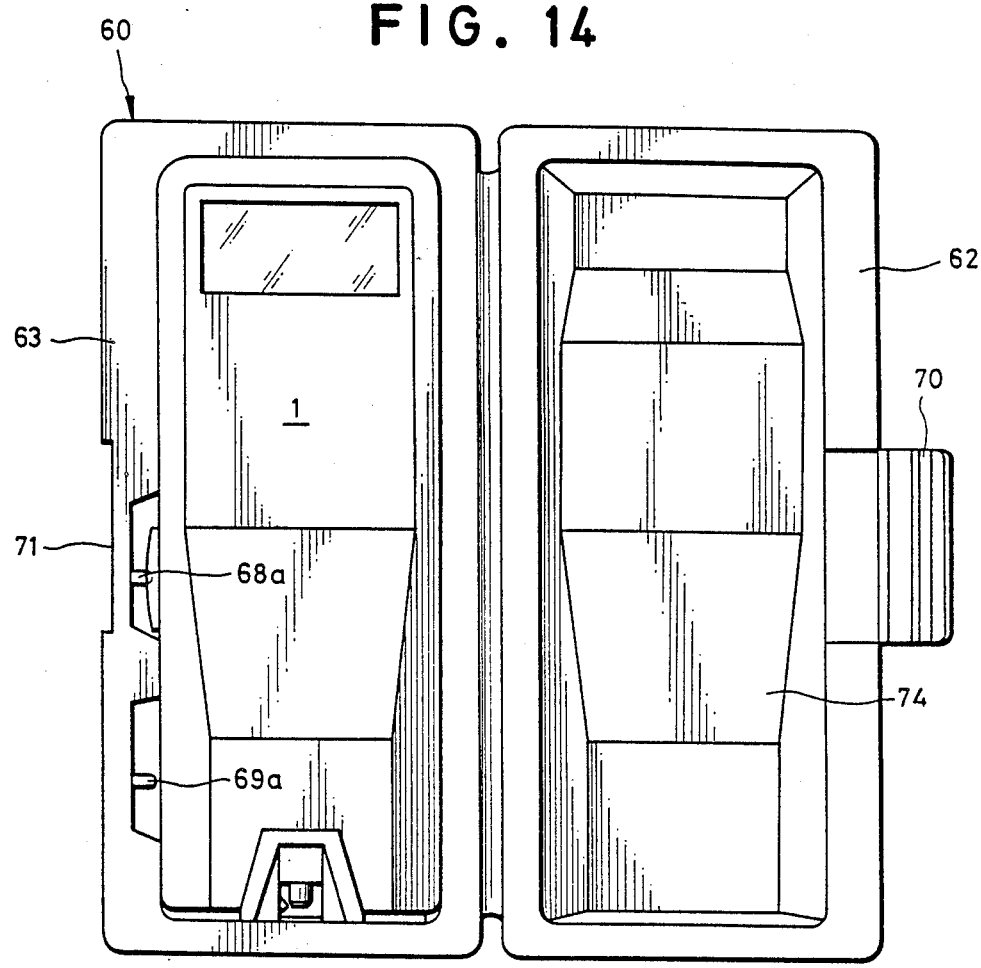
FIG. 14 is a top plan view showing the case of FIG. 12 with the densitometer of FIG. 1 arranged therein.

Referring now to FIGS. 12 to 14, a densitometer case for protection and carrying is shown. The case 60 in which the densitometer 1 shown in FIG. 1 is encased to store or carry around has a main case section 63 with a bottom board 64 onto which a high standard density plate H and a low standard density plate L are attached. For these standard density plates H and L, tile blocks are used in this embodiment. These standard density plates or blocks H and L are received within and cemented to recesses 64a and 64b, respectively, with their tops 65a and 65b flush with the upper surface of the bottom board 64. These standard density plates H and L may take various forms such as thin plates and may be formed as one plate if an accuracy deterioration is allowed.

As is seen in FIGS. 12 and 13, there are side recesses 68 and 69 formed inside the side wall 67 which receives a side wall of the densitometer 1 put on the bottom board 64 of the case 63 for a zero point correction. When inserting the side wall of the densitometer 1 into the side recess 68 or 69, the measuring aperture 32 of the densitometer 1 is located just over the high or low standard density plate H or L. Within each of these side recesses 68 and 69, there is a projection 68a, 69a which pushes and turns on the zero point correction switch 14 of the densitometer 1 when the side wall of the densitometer 1 is received in the recess 68, 69. A cover 62 is provided with an engaging projection 70 formed integrally with the cover 62 through a hinge 72, which projection is received within an engaging recess 71 formed in the outer side of the side wall 67 of the case 63. The top 74 of the cover 62 and the bottom 64 of the case 63 are shaped to accommodate the densitometer 1.

Before starting measurement when the power switch 13 is pushed to energize the densitometer 1, the densitometer 1 is shifted into the zero point correction mode of operation. Thereafter, the densitometer 1 is put on the bottom board 64 of the opened case 60 to measure the standard high or low density plate H or L. As previously described, the measuring aperture 32 of the densitometer 1 is accurately located on the high or low density plate H or L by inserting the side wall of the densitometer 1 in the side recess 68 or 69. When the side wall of the densitometer 1 is fully received, for example, in the recess 68 of the side wall 67 of the main case section 63, the measuring aperture 32 of the densitometer 1 is correctly located on the standard high density plate 64a and, simultaneously, the projection 68a pushes the zero point correction switch 14 to turn it on. As a result, the measurement starts in the previously described sequential manner.

After the use of the densitometer 1, the densitometer 1 is put in the case back side down as shown in FIG. 14 and then the cover 62 is closed. This case receives the densitometer tightly therein for the convenience of bringing around the densitometer 1.

Although the above described embodiment of the present invention is directed to a handy type densitometer which is handled by one hand, the present invention can be embodied in conventional types of densitometers such as those having a separate measuring head from a densitometer body which incorporates operation circuits, display, power source and so forth.

It will, of course, be understood that various changes and modifications may be made in the form, details, arrangement and proportion of the parts without departing from the scope of the present invention, which generally stated, consists in the matter set forth in the accompanying claims.

What is claimed is:

1. A method of measuring a reflection optical density in which a reflection density of a subject is calculated by measuring reflected light from the subject illuminated by a lamp and a part of light emanating from the lamp as a reference light, said method comprising the steps of
    energizing said lamp to emit light for a predetermined time after the start of measurement;
    measuring reflected light from a subject being measured and a reference light a plurality of times during said predetermined time to detect a plurality of measured values; and
    calculating a mean value of said plurality of measured values as a reflection optical density of the subject.

2. A method as defined in claim 1, wherein said mean value is obtained independent of maximum and minimum measured values.

3. A method as defined in claim 1, wherein said predetermined time is equal to or shorter than 0.9 sec.

4. A method as defined in claim 1, wherein said measurement of reflected light and reference light is effected four times after a predetermined time has passed from the start of energization of said lamp.

5. A portable optical densitometer, comprising
    a housing adapted to be handled by one hand;
    a measuring aperture member which is attached to a bottom of said housing so as to be placed on a subject to be measured;
    light projecting means for illuminating a said subject, said light projecting means comprising a spotlight projecting light through said measuring aperture at an angle;
    light measuring means for receiving light reflected perpendicularly from the subject through said measuring aperture;
    reference light measuring means for measuring part of the light from said light projecting means;
    a calculation circuit for calculating an optical density based on outputs from said light measuring means and said reference light measuring means;
    a display panel for display said optical density calculated by said calculation circuit; and
    a battery for supplying power to said light projecting means, said light measuring means, said reference light measuring means, said calculation circuit, and said display panel.

6. A densitometer as defined in claim 5, wherein said housing has a measuring head body with light projecting means and light receiving means incorporated therein, said head body being formed with a recess extending between its front and bottom surfaces, said measuring aperture member comprising a transparent plate containing said measuring aperture.

7. A densitometer as defined in claim 5, and further comprising
    a battery check circuit for checking a predetermined level of battery power;
    an indicator in communication with said battery check circuit, providing a visual warning indicating a change of battery power when said battery check circuit detects a battery power less than said predetermined level; and
    control means in communication with said battery check circuit, for preventing said densitometer from collecting data when said battery power is less than said predetermined level.

8. A densitometer as defined in claim 7, wherein said control means comprises an A/D converter for digitally converting optical density signals and a CPU for storing said digitally converted optical density signals in a memory, said CPU disabling said A/D converter after a predetermined interval to stop data collection.

9. A densitometer as defined in claim 7, wherein said visual warning flashes.

10. A densitometer as defined in claim 6, wherein said measuring aperture is defined by a hole shaped as an inverse frustum with its inner surface painted black.

11. A densitometer as defined in claim 10, wherein said aperture has a diameter less than approximately 2 mm.

12. A densitometer as defined in claim 11, wherein said measuring head body is made of a heat-resisting black ABS plastic material.

13. A measuring head for use in a reflection type optical densitometer, comprising
a head body member having a front and bottom opening formed by a recess extending between a bottom wall and a front wall thereof;
light projecting means incorporated in said head body member for projecting light perpendicularly to a subject which is placed under said recess, thereby to effect optical density measurement;
light measuring means for receiving light reflected from the subject;
a transparent plate attached to said bottom wall so as to cover said bottom opening; and
an aperture formed in said transparent plate at an intersection of the axes of said light projecting and light receiving means, said aperture being shaped in the form of an inverted frustum of a cone and having an inner wall painted black.

14. A measuring head as defined in claim 13, wherein said aperture has a diameter less than approximately 2 mm.

15. A measuring head as defined in claim 14, wherein said head body is made of a heat-resisting black ABS plastic material.

16. A measuring head as defined in claim 15, wherein said transparent plate is arranged flush with the bottom surface of said heady body member.

17. A case for receiving a reflection type optical densitometer therein, said case comprising a housing, a cover, and a standard optical density member mounted on at least one of said housing and cover.

18. A case as defined in claim 17, wherein said standard optical density member is provided inside of said housing.

19. A case as defined in claim 18, wherein said standard optical density member comprises a high and a low standard optical density member.

20. A case as defined in claim 19, wherein each of said high and low standard density members comprises a tile block.

21. A case as defined in claim 20, and further comprising a positioning recess formed inside said housing for receiving a part of said reflection type optical densitometer when measuring said standard density member.

22. A case as defined in claim 21, wherein said recess is provided with a projection member for operating a member which is provided on said reflection type densitometer and operated to start a measurement.

* * * * *